United States Patent [19]

Nemethy

[11] 4,346,750
[45] Aug. 31, 1982

[54] METHOD OF MAKING DENTAL BRIDGE USING A PREFABRICATED NON-PRECIOUS PONTIC

[76] Inventor: Mike Z. Nemethy, Royal Dental Lab., Inc., 3869 5th Ave. North, St. Petersburg, Fla. 33713

[21] Appl. No.: 206,292

[22] Filed: Nov. 5, 1980

Related U.S. Application Data

[62] Division of Ser. No. 42,708, May 25, 1979, Pat. No. 4,269,595.

[51] Int. Cl.³ .............................................. B22C 9/04
[52] U.S. Cl. ........................................ 164/35; 164/99
[58] Field of Search ................................... 164/34–36, 164/98–106, 246, 9, 45

[56] References Cited

U.S. PATENT DOCUMENTS 3,661,198  5/1972  Evenson .......................... 164/34 X
4,176,706  12/1979  Been ................................... 164/34

Primary Examiner—Gus T. Hampilos
Assistant Examiner—K. Y. Lin
Attorney, Agent, or Firm—Duckworth, Allen, Dyer & Pettis

[57] ABSTRACT

Disclosed is a prefabricated pontic framework formed of a non-precious material and method to be used in making dental bridges. The prefabricated pontic framework comprises a plurality of pontic supports with a connecting bar mounted on opposed sides of each pontic support, such pontic framework being selected and cut to size for a particular bridgework situation.

4 Claims, 5 Drawing Figures

METHOD OF MAKING DENTAL BRIDGE USING A PREFABRICATED NON-PRECIOUS PONTIC

This application is a division of application Ser. No. 042,708, filed May 25, 1979, now U.S. Pat. No. 4,269,595.

FIELD OF THE INVENTION

The present invention is directed to a prefabricated pontic framework formed of a non-precious material and to a method of making dental bridges using prefabricated pontic frameworks.

DESCRIPTION OF THE PRIOR ART

In manufacturing dental bridges, wax copings are formed by using cut down teeth impressions for dies. A plurality of pieces of wax or wax pontic supports are typically positioned between spaced apart abutment teeth, one such piece of wax corresponding to each missing tooth. The wax pontic supports and the wax copings are interconnected by small wax attachments. Next, the wax pieces are "invested" by surrounding the same in a substance that turns into a solid investment material. The wax copings and wax pontic framework are then placed in an oven wherein the wax is burned out. The formation of the wax pontic framework, regardless of the casting metal used, is a very time consuming step and adds greatly to the overall cost of producing dental bridges.

After the wax is burned out in the oven, a precious metal, such as gold, is centrifugally fed into the residual mold left by the departed wax. Consequently, the wax copings and wax pontics are converted to gold copings or crowns and gold pontics, each of which are interconnected by the gold alloy. It should be appreciated that the precious alloy may include other metals, such as silver. It has been preferred by prior art practices that the crowns on the abutment teeth should be of a precious alloy so as to be sufficiently malleable and burnishable to be capable of being pushed down close to the abutment tooth surfaces. As is appreciated in the art, a non-precious alloy cannot be soldered or chemically fused with a precious alloy. Hence, the formation of the dental bridge is accomplished in one casting, with the pontics, in addition to the crowns, being formed of a precious alloy. Hence, the use of a substantial quantity of precious metal, such as gold, adds tremendously to the cost of the dentist, laboratory, and patient. After the casting, porcelain is applied to the gold pontic framework and gold copings to finalize the formation of artificial teeth.

SUMMARY OF THE INVENTION

The present invention is directed to a prefabricated pontic framework formed of a non-precious material and to a method of making dental bridges using prefabricated pontic frameworks.

The prefabricated pontic frameworks comprises a plurality of pontic supports, with a pair of opposed sides of each pontic support having connecting bars extending therefrom. In one embodiment, the prefabricated pontic framework is formed of a non-precious alloy or precious alloy and in another embodiment the prefabricated pontic framework is formed of plastic. It should be appreciated that the framework can be supplied in other materials if desired, such as a gold alloy, or even wax. By providing prefabricated pontic frameworks to the dental laboratories, a substantial amount of time for the technician is saved in making the dental bridges, in that the prior art practice requires the pontic framework to be made of wax prior to casting. Secondly, the prefabricated pontic framework allows for the replacement of gold alloy pontic supports with the prefabricated non-precious pontic framework, thereby reducing cost to the dentist, laboratory, and patient. The use of the plastic prefabricated pontic framework allows for the pontic framework to be heated and bent to conform to a severely swayed or curved edentulous ridge, such as that encountered with making anterior bridges. Moreover, due to the strength of and rigidity of pontic framework formed of non-precious alloys, the dimensions of the pontic framework can be decreased as compared to the gold alloy pontic framework of the prior art. This, in turn, allows for increased room for porcelain, thereby providing improved esthetics in the porcelain bridgework.

The proposed method of making dental bridges comprises cutting the prefabricated pontic framework to the desired length for fitting between opposed abutment dies, with the desired number of pontic supports corresponding to the missing teeth. Next, the cut pontic framework is attached to a pair of wax copings, which are shaped on the abutment dies. Subsequently, the prefabricated pontic framework, with at least one wax coping on each end thereof, is invested and cast. This method provides a dental bridge frame having either non-precious or gold copings or crowns which are mechanically bonded to the prefabricated pontic framework. Since non-precious alloys are not readily burnishable, the method allows for the use of gold alloy copings with non-precious pontic framework. Hence, the gold alloy coping is sufficiently malleable to meet the needs of conforming to the abutment teeth, whereas the pontic framework is sufficiently strong and rigid to provide structural support. At the same time, as previously explained, the use of the prefabricated pontic framework reduces gold usage and saves time for the technician by eliminating the prior art practice of "waxing up" the pontic framework. That is, making them "from scratch" is eliminated.

BRIEF DESCRIPTION OF THE DRAWINGS

Further objects and advantages of the present invention will become apparent as the following description proceeds, taken in conjunction with the accompanying drawings in which.

DESCRIPTION OF THE PREFERRED EMBODIMENT

Figure 1:
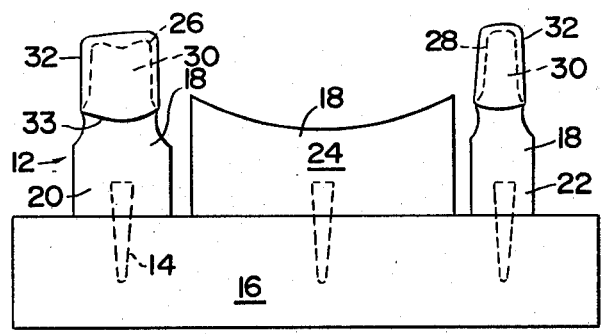
FIG. 1 is a plan view of the initial stages of forming a dental bridge in the prior art with the illustrated elements being found in the present invention.

FIG. 1 illustrates the initial steps and elements in making dental bridges which are found in the prior art and which are in common with the present invention.

Figure 3:
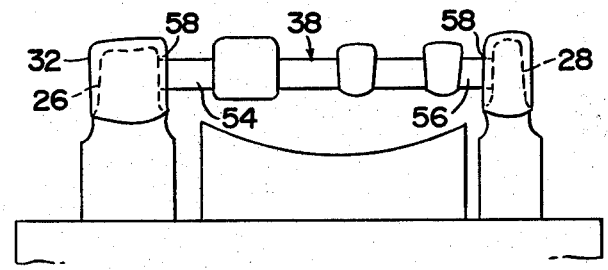
FIG. 3 illustrates the "waxing up" of the present invention.
Figure 4:
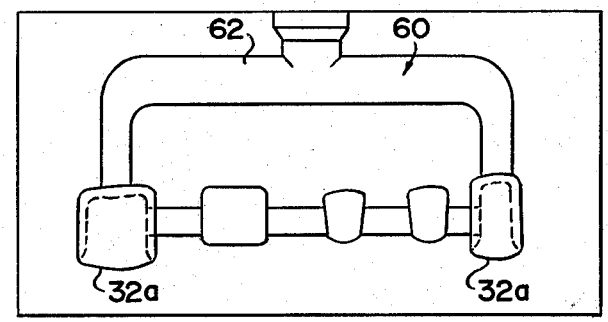
FIG. 4 illustrates the casting and "burn out" of the wax of the present invention.
Figure 5:
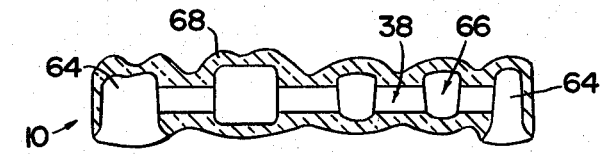
FIG. 5 illustrates the final dental bridge of the present invention.

FIGS. 2 through 5 progressively illustrate the successive steps in forming the dental bridge of the present invention, with a completed dental bridge 10 being illustrated in FIG. 5.

The dental bridge 10 is used to mount one or more artificial teeth between adjoining, real abutment teeth.

Referring to FIG. 1, a positive impression mold die 12, which is normally prepared from a negative impression provided from a dental office, is prepared in a conventional manner, typically in a dental laboratory. As is standard practice, the impression mold die 12 is made of hardened die stone, with a plurality of keyed pins 14 being used for anchoring the impression mold die 12 into a support base 16. Next, the prior art practice calls for cutting the impression mold die 12 to create a plurality of sections 18. Typically, there are abutment teeth sections 20 and 22, which define abutment dies 26 and 28 respectively, and a center edentulous section 24, which corresponds to the location of the missing teeth. It should be understood that the abutment dies 26 and 28 conform to the image of the real abutment teeth after they have been cut down around an end tooth area which, in turn, defines an end tooth portion 30 of the dies 26 and 28. The abutment teeth dies 26 and 28, in a conventional manner, are then "waxed-up" to produce wax coping 32, which are thin wax molds that conform to the exterior of the cut down tooth portions 30 of the abutment dies 26 and 28. The wax copings 32 are normally trimmed to terminate at a margin 33, which corresponds to the edge of the cutdown tooth portion 30 of the abutment teeth dies 26 and 28. In other words, the tooth portions 30 of abutment dies 26 and 28 form the wax copings 32. There may be more than one abutment die on each side of the dental bridge 10. Up to this point, the prior art practice and the processes of this invention are the same. The remainder of the prior art practice is described in the Background Section.

Figure 2:
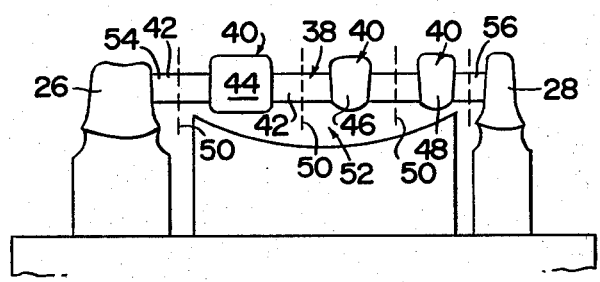
FIG. 2 is a plan view of the initial stages of forming a dental bridge of the present invention wherein the cut prefabricated pontic framework of the present invention is illustrated.

The improvement of the present invention comprises replacing the precious alloy pontic framework of the prior art with a prefabricated non-precious pontics framework 38, while retaining copings or crowns for the abutment teeth formed of precious metal. Also, the copings or crowns for the abutment teeth can be cast in either precious or non-precious metal as desired by the dentist. Referring to FIG. 2, the method of the present invention continues from those steps heretofore described in relation to the prior art in a manner illustrated in FIG. 2. More specifically, before the wax copings 32 are waxed-up using conventional wax-up procedures, the prefabricated pontic framework 38 is cut to size. It is contemplated that the prefabricated pontic framework 38 will be supplied by a dental manufacturer to the dental laboratories in a form described hereinafter. The prefabricated pontic framework of the preferred embodiment 38 comprises three pontic supports 40 interconnected by a plurality of knurled connecting bars 42, one such bar 42 being disposed on opposed sides of each of the pontic supports 40. The illustrative example of FIG. 2 shows the pontic framework 38 which corresponds to a desired dental bridge for replacing one molar tooth, using molar pontic support 44, and two bicuspid teeth, using biscuspid pontics support 46 and 48. This defines a three unit posterior pontic framework 38. If less than the three pontic supports 44, 46 and 48 are required, it is contemplated that the connecting bars 42 can be transversely cut using conventional cutting methods to give the desired pontic framework 38. Consequently, the pontic framework 38 can, for example, be divided up along cut lines 50 so as to provide a pontic framework 38 cut to any length according to the patient case requirements, utilizing one, two, or all three pontic supports 40. The pontic framework 38 is ideally composed of a non-precious alloy, such as chrome cobalt, or alternatively a plastic or wax. It should be appreciated that the prefabricated pontic framework 38 can be provided with any number of pontic supports 40, although three are preferable. Moreover, the pontic framework 38 can be designed to correspond to any part of a patient's teeth. It is anticipated that at least six or seven different pontic frameworks 38 will be provided to the dental laboratories from the dental manufacturers. This range of pontic frameworks 38 will cover all or most of the possible dental bridges 10 that are normally required. It is contemplated that the pontic framework 38 will have various combinations of pontic supports 40, with there being a size range, such as large, medium, and small, depending upon the type and size of the missing tooth to which the individual pontic support 40 corresponds. Moreover, the individual pontic supports 40 can be ground to meet a desired size and configuration.

Referring to FIG. 2, after the dental laboratory has selected the particular pontic framework 38 for the desired dental bridge 10, the pontic framework 38 is cut to fit an edentulous space 52, which corresponds to the space between the abutment teeth dies 26 and 28. The two connecting bars, that protrude from the ends of the pontic framework 38 and which engage the wax copings 32, are defined as the distal bar 54 and the mesial bar 56. Hence, these bars 54 and 56 are cut so that they are close to or touching the appropriate abutment dies 26 and 28. Preferably, the dimensional length of the pontic frame 38 is determined prior to the abutment dies 26 and 28 being waxed up. After the abutment dies 26 and 28 are waxed up, the tolerance therebetween normally does not permit the cut pontic arrangement 38 to be fitted therebetween. Preferably, the pontic arrangement 38 can be heated up so that the wax copings 32 will melt slightly in the areas of contact with the pontic framework 38. This permits the pontic framework 38 to be positioned in its correct location. Other procedures for positioning the pontic framework 38 will be obvious to one skilled in the art, such as trimming away a portion of the wax coping 32, instead of melting it away.

Referring to FIG. 3, the next step of the process is to flow wax 58 around the connecting bars 54 and 56 so as to connect the pontic framework 38 securely to the opposed pair of wax copings 32. It should be appreciated that the connecting bars 54 and 56 allow adequate mechanical retention for the wax 58.

Referring to FIG. 4, the next step, after pouring the wax 58, is to invest the entire bridge framework, which at this point comprises the pontic framework 38 with the pair of opposed wax copings 32 mounted on each end thereof by the wax 58. The entire bridge framework is removably mounted on a relatively heavy, horizontally disposed sprue 60. In that the plastic sprue 60 has a hollow tube portion 62 therein, the sprue 62 serves not only to stabilize the entire bridge framework, but it also serves as a reservoir to provide interior access for the input of the material to replace the wax. Hence, in a conventional manner the entire bridge framework is surrounded by known liquid investment material, which then hardens. Then the wax copings 32, the wax 58 and the sprue 62 are burned out in an oven, typically at 1200 degrees Fahrenheit. Subsequently, the investment material has hollow areas which previously held the wax and into which the melted alloy, such as gold or non-precious metal is centrifugally fed, in a manner well known in the art, to produce the entire bridge framework in metal. The spaces previously occupied by the wax become crowns or metal copings 32, which are mechanically attached to the pontic framework 38. It should be appreciated that as part of the prior art practice, it is well known that the coefficient of expansion of the gold and its surrounding investment material needs to be similar, so as to avoid various shrinkage problems. As with the prior art, the expansion of gold for the crowns or copings 32 is controlled. With the prefabricated pontic framework 38, there is no expansion or contraction thereof; hence, the shrinkage problem with respect to the framework 38 is virtually eliminated. As is well known in the art, soldering of precious metal to non-precious metal is not possible. However, with the above described investing and casting procedures, a mechanical bond is formed between the non-precious pontic framework 38 and the precious or non-precious crowns or pontics 32.

In the preferred embodiment the wax copings 32 are replaced with a precious alloy, such as a gold alloy, for the reason that it is readily burnishable. However, a non-precious material identical to the prefabricated pontic arrangement 38 can also be used for the copings 32, depending upon the dentist's specifications. The non-precious alloys are inherently stronger and more rigid that the softer and more pliable gold alloys. Gold alloy pontics have a tendency to flex under stress, whereas those of non-precious alloy are more stable. Hence, it has proven very desirable to make the crowns out of precious alloys so that they can be burnished to fit the abutment teeth. On the other hand, it has proven to be very desirable to make the pontic framework 38 out of a non-precious alloy so as to provide structural support strength. Moreover, due to the strength of and rigidity of the non-precious pontic framework 38, the dimensions of the pontic framework 38 can be decreased as compared to those composed of a precious alloy. As will become apparent hereinafter, this, in turn, allows for increased room for porcelain, thereby improving the esthetics in the porcelain bridgework. In summary, since the non-precious alloys are not readily burnishable, the prefabricated pontic framework 38 allows for the use of gold copings or crowns 32 with non-precious pontic frameworks. This overcomes the problem of non-burnishable margins for the metal copings that would occur with a full non-precious bridge 10. At the same time, the replacing of gold alloy pontics with prefabricated non-precious pontic frameworks 38 results in a substantial cut in gold alloy usage, thereby reducing cost to the dentist, laboratory, and patient. However, the manufacturer can also supply gold alloy pontic frameworks if the dentist requires it.

Referring to FIG. 5, after the above described casting step the wax copings 32 have been converted to metal copings 64 and at this point consists of an incomplete dental bridge framework 66. This dental bridge framework 66, consisting of the prefabricated framework 38 with metal copings 64 attached thereto, is then finished down following normal, well-known procedures. Porcelain 68 is then applied to the dental bridge framework 66 to give the appearance and form of real teeth. Some non-precious alloys require a porcelain bonding agent be used before application of the standardly applied opaque porcelain. In the case where a bonding agent is used and the copings 64 are of gold alloy, de-gassing of the gold alloy may be obtained while firing the bonding agent. Opaque porcelain and translucent porcelain are then applied using conventional porcelain-to-metal bridgework procedures.

In an alternative embodiment of the present invention, the prefabricated pontic framework 38 can be composed of a plastic or wax material. This is particularly desirable in the case where the dental bridge 10 is being made for an edentulous ridge which is severely swayed or curved. This situation requires more extensive pontic adaption, such as with anterior dental bridges 10. A prefabricated pontic framework 38 formed of plastic or wax can be heated and curved to the desired dimensions to meet the severely curved edentulous ridge. Moreover, the plastic pontic framework 38, in turn, can then be used to cast a non-precious or precious alloy pontic framework 38. In other words, the plastic pontic framework, after being properly bent, can be burned away, with a non-precious or precious material being substituted therefor. In summary, a plastic pontic framework 38 can be desirable in an anterior bridge situation, while a non-precious alloy pontic framework can be desirable in a posterior bridge situation.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A method of making dental bridges wherein at least a pair of opposed wax copings, formed by at least a pair of opposed abutment dies, are subsequently invested and cast into precious alloy copings, the improvement comprising the steps of:
   providing a prefabricated pontic framework of non-precious metal having at least one pontic support with a pair of connecting bars extending therefrom;
   cutting the connecting bars to a desired length to fit between the abutment dies of said pair of opposed abutment dies;
   attaching one of the connecting bars to each of the wax copings of said pair of opposed wax copings;
   investing the pair of opposed wax copings with the prefabricated pontic framework disposed therebetween.

2. In the method of claim 1,
   providing a prefabricated pontic framework formed of a non-precious alloy.

3. In the method of claim 1,
   providing a plurality of pontic supports rigidly connected to each other with the connecting bars;
   providing the prefabricated pontic framework with a pair of connecting bars extending from each end of the prefabricated pontic framework;
   cutting the prefabricated pontic framework across one of connecting bars to obtain the desired number of pontic supports of the desired size.

4. In the method of claim 1,
   mounting the pair of opposed copings, having the prefabricated pontic framework therebetween, on a prong-like sprue;
   casting the pair of opposed wax coping and union to the framework in a precious alloy.

* * * * *